(12) United States Patent
Sun (10) Patent No.: US 11,428,768 B2
(45) Date of Patent: Aug. 30, 2022

(54) CHEMICAL EXCHANGE SATURATION TRANSFER MAGNETIC RESONANCE IMAGING WITH GATING SYNCHRONIZED ACQUISITION

(71) Applicant: The General Hospital Corporation, Boston, MA (US)

(72) Inventor: Phillip Zhe Sun, Woburn, MA (US)

(73) Assignee: The General Hospital Corporation, Boston, MA (US)

( * ) Notice: Subject to any disclaimer, the term of this patent is extended or adjusted under 35 U.S.C. 154(b) by 427 days.

(21) Appl. No.: 15/946,491

(22) Filed: Apr. 5, 2018

(65) Prior Publication Data

US 2018/0292495 A1 Oct. 11, 2018

Related U.S. Application Data

(60) Provisional application No. 62/481,745, filed on Apr. 5, 2017.

(51) Int. Cl.
*A61B 5/055* (2006.01)
*G01R 33/56* (2006.01)
(Continued)

(52) U.S. Cl.
CPC .......... *G01R 33/5605* (2013.01); *A61B 5/055* (2013.01); *A61B 5/7285* (2013.01);
(Continued)

(58) Field of Classification Search
None
See application file for complete search history.

(56) References Cited

U.S. PATENT DOCUMENTS

| 5,000,182 A | * | 3/1991 | Hinks | ..................... A61B 5/352 600/413 |
| 6,943,033 B2 | | 9/2005 | Van Zijl et al. | |

(Continued)

OTHER PUBLICATIONS

Pumphrey et al., "Advanced cardiac chemical exchange saturation transfer (cardioCEST) MRI for in vivo cell tracking and metabolic imaging" NMR in Biomedicine. vol. 29, Issue 1, Jan. 2016, pp. 74-83 and, published online with author provided supplemental information Dec. 18, 2015 (Year: 2016).*

(Continued)

*Primary Examiner* — Colin T. Sakamoto
(74) *Attorney, Agent, or Firm* — Quarles & Brady LLP (57) ABSTRACT

Methods and systems for producing a magnetic resonance (MR) image of a subject include acquiring a first physiological monitoring signal related to a first physiological process of the subject and acquiring a second physiological monitoring signal related to a second physiological process of the subject. The method also includes analyzing the first physiological monitoring signal and the second physiological monitoring signal to identify at least a first trigger point and a second trigger point and, upon identifying the first trigger point, applying a radiofrequency (RF) saturation module at a selected frequency to saturate a selected spin species in the subject. Upon identifying the second trigger point, the method includes performing a chemical exchange striation transfer (CEST) readout to acquire CEST data and then reconstructing the CEST data to produce a CEST image of the subject.

18 Claims, 7 Drawing Sheets
(5 of 7 Drawing Sheet(s) Filed in Color)

(51) Int. Cl.
  *G01R 33/567* (2006.01)
  *G01R 33/483* (2006.01)
  *G01R 33/563* (2006.01)
  *A61B 5/00* (2006.01)
  *A61B 5/08* (2006.01)
  *A61B 5/352* (2021.01)

(52) U.S. Cl.
  CPC ..... *G01R 33/4835* (2013.01); *G01R 33/5673* (2013.01); *G01R 33/56366* (2013.01); *A61B 5/0816* (2013.01); *A61B 5/352* (2021.01)

(56) References Cited

U.S. PATENT DOCUMENTS

| | | | | |
|---|---|---|---|---|
| 7,769,430 | B2 * | 8/2010 | Mostafavi | A61B 6/541 |
| | | | | 600/428 |
| 2003/0036694 | A1 * | 2/2003 | Liu | G01R 33/563 |
| | | | | 600/413 |
| 2003/0161436 | A1 * | 8/2003 | Boyd | A61B 6/504 |
| | | | | 378/8 |
| 2005/0113670 | A1 * | 5/2005 | Salla | A61B 5/113 |
| | | | | 600/413 |
| 2005/0113672 | A1 * | 5/2005 | Salla | A61B 5/0037 |
| | | | | 600/413 |
| 2005/0201510 | A1 * | 9/2005 | Mostafavi | A61B 6/463 |
| | | | | 378/8 |
| 2007/0038069 | A1 * | 2/2007 | Itagaki | G01R 33/563 |
| | | | | 600/410 |
| 2007/0069726 | A1 * | 3/2007 | Miyoshi | G01R 33/5635 |
| | | | | 324/307 |
| 2008/0154121 | A1 * | 6/2008 | Kouwenhoven | G01R 33/5673 |
| | | | | 600/413 |
| 2008/0284427 | A1 * | 11/2008 | van Zijl | A61B 6/481 |
| | | | | 324/307 |
| 2010/0308823 | A1 * | 12/2010 | Sugiura | G01R 33/56316 |
| | | | | 324/309 |
| 2013/0338487 | A1 * | 12/2013 | Kassai | A61B 5/7285 |
| | | | | 600/413 |
| 2014/0039297 | A1 * | 2/2014 | Keupp | G01R 33/5673 |
| | | | | 600/413 |
| 2014/0117987 | A1 * | 5/2014 | Yui | G01R 33/5605 |
| | | | | 324/309 |
| 2016/0091443 | A1 * | 3/2016 | Bar-Shir | G01N 24/08 |
| | | | | 436/79 |
| 2017/0086736 | A1 * | 3/2017 | Liu | G01R 33/5605 |

OTHER PUBLICATIONS mriquestions.com "Intro to Gating/Trigger: How are cardiac and respiratory gating performed?" archived on Feb. 11, 2016, retrieved from <https://web.archive.org/web/20160211183447/http://mriquestions.com/gating-methods.html> on Jul. 13, 2020 (Year: 2016).*

Schmitter et al., "Simultaneous Multislice Imaging in Dynamic Cardiac MRI at 7T Using Parallel Transmission" Magnetic Resonance in Medicine. vol. 77, Issue 3, Mar. 2017, pp. 1010-1020, published online on Mar. 7, 2016 (Year: 2016).*

Sun et al. "Simulation and optimization of pulsed radio frequency irradiation scheme for chemical exchange saturation transfer (CEST) MRI—demonstration of pH-weighted pulsed-amide proton CEST MRI in an animal model of acute cerebral ischemia" Imaging Methodology, 66, 4, Oct. 2011, p. 1042-1048, Mar. 24, 2011 (Year: 2011).*

Wu et al., "An overview of CEST MRI for non-MR physicists" EJNMMI Physics, 3, 19 (2016) (Year: 2016).*

Zhou et al., Using the Amide Proton Signals of Intracellular Proteins and Peptides to Detect pH Effects in MRI, Nature Medicine, 2003, 9(8):1085-1090.

\* cited by examiner

CHEMICAL EXCHANGE SATURATION TRANSFER MAGNETIC RESONANCE IMAGING WITH GATING SYNCHRONIZED ACQUISITION

CROSS-REFERENCE TO RELATED APPLICATIONS

This application is based on, claims the benefit of, and incorporates herein by reference, U.S. Provisional Patent Application 62/481,745, filed Apr. 5, 2017.

STATEMENT REGARDING FEDERALLY SPONSORED RESEARCH

This invention was made with government support under 1R01NS083654 awarded by the National Institutes of Health. The government has certain rights in the invention.

BACKGROUND

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M^z$, may be rotated, or "tipped," into the x-y plane to produce a net transverse magnetic moment $M_{xy}$. A signal is emitted by the excited nuclei or "spins," after the excitation signal $B_1$ is terminated, and this signal may be received and processed to form an image.

When utilizing these magnetic resonance (MR) or nuclear magnetic resonance (NMR) signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well-known reconstruction techniques.

The measurement cycle used to acquire each MR signal is performed under the direction of a pulse sequence produced by a pulse sequencer. Clinically available magnetic resonance imaging (MRI) systems store a library of such pulse sequences that can be prescribed to meet the needs of many different clinical applications. Research MRI systems include a library of clinically-proven pulse sequences and they also enable the development of new pulse sequences.

Coronary artery disease and myocardial infarction (MI) results in about 15% of all deaths in the United States, causing an immense health and socioeconomic burden. Although myocardial perfusion imaging (MPI) has played a key role in diagnosing cardiovascular disease, it mainly depicts blood flow status, providing limited characterization of ischemic tissue status. Toward this goal, myocardial T2 MRI has shown sensitivity to myocardial edema, and its mismatch with late gadolinium enhanced (LGE) MRI has been postulated to approximate area at risk (AAR). Yet, there has been some controversies in the diagnostic value of cardiac T2 imaging, particularly the time course/degree of edema formation, the pathophysiological relationship between edema and ischemia, and importantly its sensitivity and specificity to AAR.

Toward this goal, myocardial metabolic measurements of high-energy phosphates (e.g., phosphocreatine) and pH have shown some promise for identification of early myocardial infarction. Acidosis is an informative biomarker of ischemia conditions. It has been noted that myocardium ischemia and acute stroke in brain share similar pathophysiology. In brain, acidosis is closely associated with oxygen/glucose metabolism, which served as a metabolic imaging biomarker for defining salvageable ischemic tissue (penumbra). In a classic set of studies in the early 1990s, investigators at the Mayo Clinic used optical imaging in rabbits to show that pH changes had greater power to define penumbral tissue than blood flow measurements. Acidosis appeared to be detrimental in cardiac contractile failure. Indeed, Camacho reported that inorganic phosphate level increases and intracellular pH (pHi) decreases quickly following ischemia. On the other hand, it takes much longer for phosphocreatine level to decrease with insignificant change in adenosine triphosphate (ATP) level. In an editorial, Katz pointed out that the lactic acid production increases fifty times within less than a minute in the ischemic heart. He further postulated that acidotic state displaces calcium bound to troponin, resulting in fewer points of releases of the inhibition of the actin-myosin interaction. Such evidence strongly suggested that pH is a particularly attractive biomarker for providing information of contractile response from dysfunctional, but viable myocardial regions in MI. However, phosphorus (31P) MR spectroscopy is challenging technically with coarse spatiotemporal resolution, limiting its routine use in the clinical setting.

Therefore, it would be desirable to develop cardiac pH analysis techniques that non-invasively provide the necessary clinical information.

SUMMARY OF THE PRESENT DISCLOSURE

The present disclosure provides systems and methods for producing a magnetic resonance (MR) image of a subject. In one aspect, a method is provided that includes acquiring a first physiological monitoring signal related to a first physiological process of the subject and acquiring a second physiological monitoring signal related to a second physiological process of the subject. The method also includes analyzing the first physiological monitoring signal and the second physiological monitoring signal to identify at least a first trigger point and a second trigger point and, upon identifying the first trigger point, applying a radiofrequency (RF) saturation module at a selected frequency to saturate a selected spin species in the subject. Upon identifying the second trigger point, the method includes performing a chemical exchange striation transfer (CEST) readout to acquire CEST data and then reconstructing the CEST data to produce a CEST image of the subject.

In another aspect of the present disclosure, a system is provided that includes a magnet system configured to generate a polarizing magnetic field about at least a portion of a subject and a magnetic gradient system including a plurality of magnetic gradient coils configured to apply at least one magnetic gradient field to the polarizing magnetic field. The system also includes a radio frequency (RF) system configured to apply an RF field to the subject and to receive magnetic resonance signals from the subject using a coil array and computer system. The computer system is programmed to analyze a first physiological monitoring signal related to a first physiological process of the subject and a second physiological monitoring signal related to a second physiological process of the subject to identify at least a first trigger point and a second trigger point. Upon identifying the first trigger point, the computer system is configured to control the RF system to applying a radiofrequency (RF) saturation module at a selected frequency to saturate a selected spin species in the subject and, upon identifying an occurrence of the second trigger point, control the magnetic gradient system and the RF system to perform acquire data from the subject. The computer system is then configured to reconstruct the data to produce an image of the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PRESENT DISCLOSURE

The MR or signals acquired with an MRI system are signal samples of the subject of the examination in Fourier space, or what is often referred to in the art as "k-space." The MR or NMR signals can be used to measure the exchange of magnetization between molecules to provide unique information about the chemical and molecular environment of samples or tissues. One type of such exchange measurement is broadly referred to in the field as magnetization transfer. This technique is capable of measuring the exchange of magnetization from spin species that have short transverse relaxation times ($T_2$). Because many different molecules have a short $T_2$, this technique is not particularly specific.

A second type of magnetization exchange occurs between water protons and a molecule with long enough $T_2$ that its difference in frequency from water can be observed. Saturation of the magnetization from this molecule will generally decrease the measurable signal from water. This effect is generally referred to in the field as chemical exchange saturation transfer ("CEST"). Two different types of molecules can generate CEST effects: endogenous, or naturally occurring, molecules and exogenous contrast agents. In either instance, the molecules whose chemical exchange with water produces the CEST effect are generally referred to as so-called "exchangeable protons."

The CEST imaging method offers three advantages over traditional molecular MRI techniques. First, in some cases the molecules of interest within the subject can be directly detected. This feature mitigates the need for administering contrast agents to the subject. Second, the image contrast mechanism can be controlled with the RF pulses produced by the MRI system and, as such, can be turned on and off when desired. This control allows the location of specific molecules of interest to be detected by comparing images having the desired contrast present to those where it has been turned off. Lastly, the CEST imaging method is far more sensitive than traditional molecular MRI techniques, making it able to detect substantially low concentrations of given molecules.

Measuring the exchange of magnetization between molecules with nuclear magnetic resonance can provide unique information about the chemical and molecular environment of samples or tissues. CEST imaging renders MRI, which usually detects only bulk water signal, sensitive to metabolites and their byproducts, such as glucose and lactate. The CEST imaging method is built upon the method of conventional magnetization transfer. The CEST contrast is achieved by the selective irradiation of labile protons, which in turn attenuate the bulk water signal through saturation transfer. Labile protons are saturated using either an off-resonance pulse or continuous wave of RF irradiation. This saturation process is known as "RF labeling" or simply "labeling". It is the transfer of this saturation through chemical exchanges between the exchangeable and water protons that forms the basis of CEST imaging methods.

In particular, frequency-dependent saturation effects are visualized similar to conventional magnetization transfer (MT) spectra by plotting the water saturation, often normalized by the signal without saturation, as a function of saturation frequency. This gives what has been dubbed a "Z spectrum" or the "CEST spectrum."

The size of the CEST effect is determined by how quickly the protons exchange their magnetization with water. This exchange rate is believed to be determined by pH, so the CEST effect can also potentially provide information indicative of altered pH levels. The chemical exchange between bulk water and amide protons from endogenous proteins and peptides has been shown to be sensitive to ischemic tissue acidosis, and as a result has given rise to an imaging technique referred to as amide proton transfer (APT) imaging. Conventional APT imaging methods are described, for example, by J. Zhou, et al., in "Using the Amide Proton Signals of Intracellular Proteins and Peptides to Detect pH Effects in MRI," Nature Medicine, 2003; 9:1085-1090, and in U.S. Pat. No. 6,943,033. Since tissue pH decreases in response to abnormal glucose/oxygen metabolism during acute ischemia, pH-sensitive APT imaging may serve as a surrogate metabolic imaging marker for stroke. In that it complements perfusion and diffusion MRI, APT imaging may allow better characterization of penumbra for predicting ischemic tissue outcome in acute stroke.

Figure 1A:
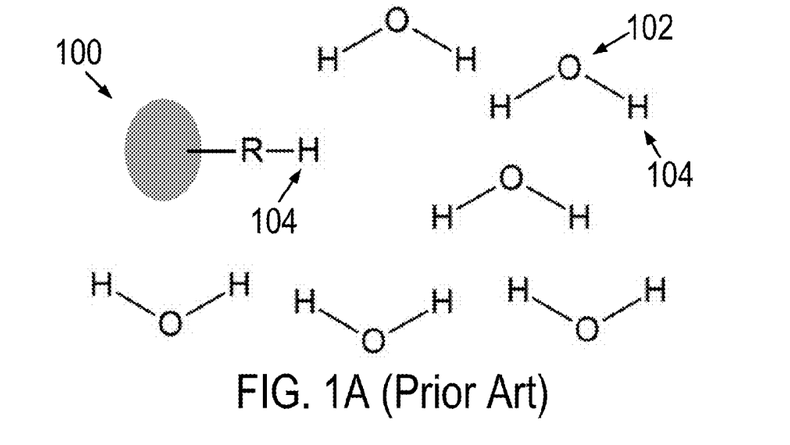
FIG. 1A is a schematic illustration of a small quantity of metabolite dissolved in a solvent, where each of the metabolite and the solvent include exchangeable protons in chemical exchange.
Figure 1B:
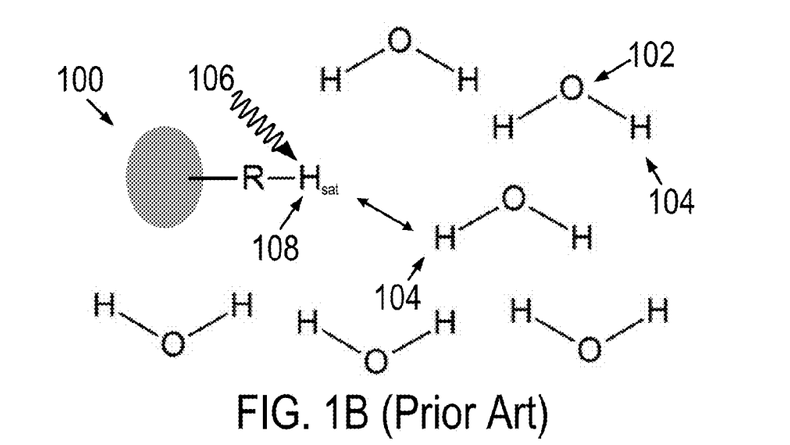
FIG. 1B is a schematic illustration of an RF pulse being applied to the exchangeable proton on the metabolite to form a saturated proton, where the saturated proton is in chemical exchange with the solvent.
Figure 1C:
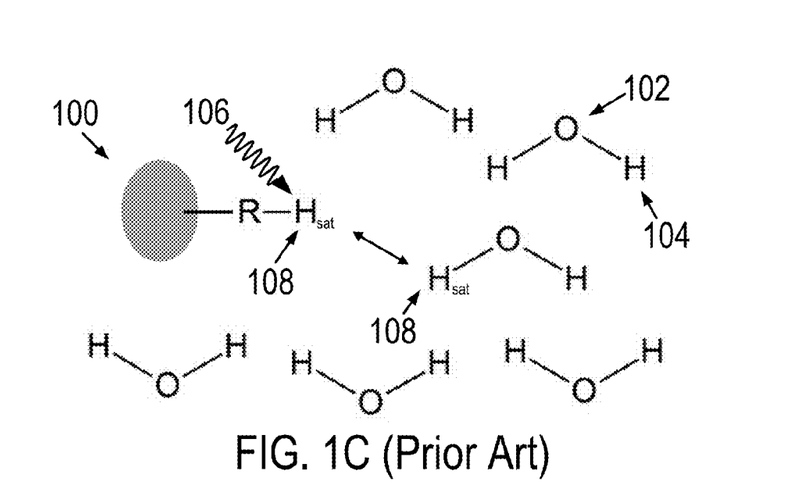
FIG. 1C is a schematic illustration of the saturated proton being transferred to the solvent resulting in a loss of solvent signal over time.

Referring now to FIGS. 1A-1C, a schematic illustration is shown to illustrate magnetization transfer via chemical exchange between a metabolite and a bulk solvent solution, which is exploited to achieve CEST contrast. FIG. 1A shows a metabolite 100 dissolved in a solvent 102 where both the metabolite 100 and the solvent 102 comprise an exchangeable proton 104. FIG. 1B shows an exchangeable proton 104 being selectively saturated by an RF pulse 106 to produce a saturated proton 108. Magnetic saturation will spontaneously be transferred to the solvent 102 overtime due to chemical exchange/through space magnetization transfer of the saturated proton 108 with the exchangeable protons 104. This process continues to produce a reduction in the solvent 102 signal over time, which may be detected using MR imaging. The loss of solvent 102 signal provides an indirect measure for the concentration of the metabolite 100 in the solution, which may be visualized from the variation in the solvent 102 signal as a function of offset frequency of the irradiation pulse, known as a Z-spectrum. CEST imaging has been demonstrated in mapping low-concentration endogenous metabolites 100 with exchangeable protons 104 such as metabolites 100 with amide (—NH), amine (NH$_2$) and hydroxyl (—OH) functional groups. Typically, the solvent 102 comprises water, but could conceivably be any solvent 102 that includes an exchangeable proton 104.

A number of different molecular groups have been suggested for CEST studies. One such group are the amide protons. Amide protons are present in large numbers on peptides and proteins; therefore, amide proton CEST should be reflective of protein concentration in cells. Other exchangeable protons include those protons contained in hydroxyl and glycogen, as well as paramagnetic molecules in general. It will be appreciated by those skilled in the art that the methods described herein are applicable not only to amide proton CEST, but also for CEST imaging techniques that utilize other molecular targets, such as glycogen ("glycoCEST"), hydroxyl proton CEST ("OH CEST"), and paramagnetic molecule CEST ("paraCEST"). The term "labile proton" or "exchangeable proton" herein refers to those proton or other molecular targets from which magnetization or saturation is desired to transfer to water protons during a CEST imaging scan.

As suggested, CEST MRI is a sensitive imaging technique for detecting compounds containing exchangeable protons. Such labile protons can be selectively saturated by an RF pulse, and the saturation subsequently transferred to the bulk water signal via proton chemical exchange, resulting in substantial sensitivity enhancement. CEST imaging has been demonstrated in mapping low-concentration metabolites such as creatine (Cr), glucose, glutamate, and changes in microenvironment properties such as temperature and pH, promising a host of in vivo applications such as imaging of ischemic stroke and tumor.

Figure 2A:
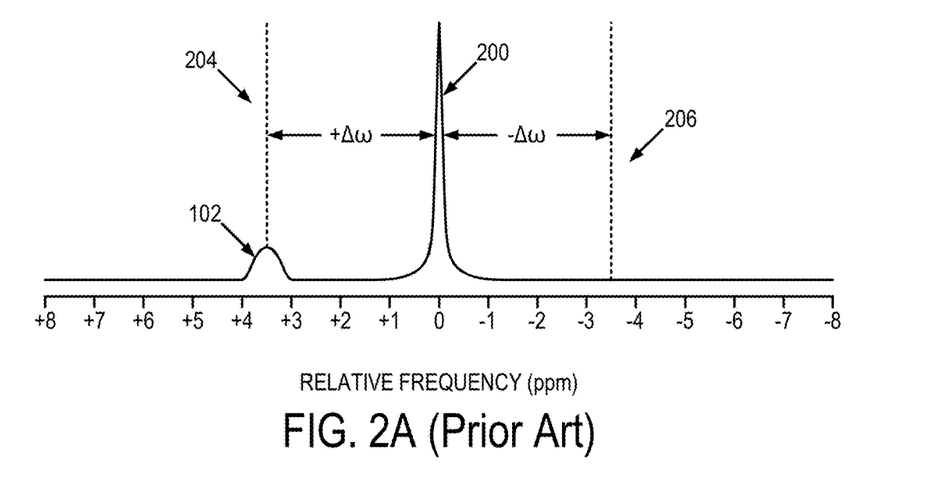
FIG. 2A is a graphic illustrations of an exemplary frequency spectrum that includes a water proton resonance peak and an amide proton resonance peak, which is only one specific example of the more general group of other labile protons groups and semisolid macromolecules.
Figure 2B:
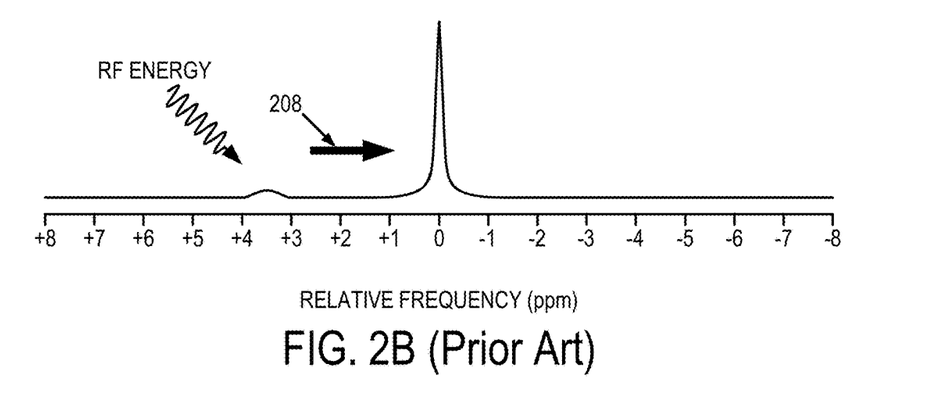
FIG. 2B is a graphic illustration of the effect of the application of radio frequency ("RF") energy at a labeling frequency that is around the resonance frequency of an exchangeable proton, such as an amide proton, on detectable signal from water protons adjacent the exchangeable proton.
Figure 2C:
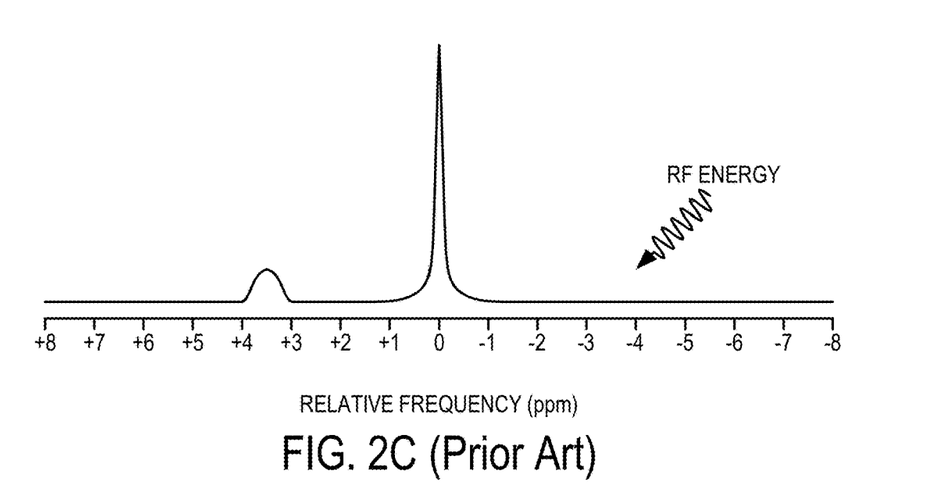
FIG. 2C is a graphic illustration of the effect of the application of RF energy at a reference frequency, equal to the negative of the labeling frequency, on detectable signal from water protons adjacent the exchangeable proton.

Referring now to FIGS. 2A-2C, a graphic illustration of an exemplary method for producing a CEST Z spectrum is shown. An exemplary Z spectrum is illustrated in FIG. 2A, where the spectrum includes a spectral peak 200 corresponding to water protons and a spectral peak 202 corresponding to amide protons. The amide proton peak 202 exists at a frequency shift relative to the water peak 200. For example, there is a frequency shift of around +3.5 parts per million ("ppm") between the water peak 200 and the amide proton peak 102. Thus, a so-called "labeling spectral line" 204, or "labeling frequency," is centered at or around the resonance frequency of the exchangeable proton, which for an amide proton is shifted about +3.5 ppm relative to the water peak 200. In general, for CEST imaging, the labeling spectral line is selected as a frequency at or around the resonance frequency of the exchangeable proton. A so-called "reference spectral line" 206, or "reference frequency," also exists, and is equal to the negative of the labeling frequency relative to the water peak 200.

To obtain a Z-spectrum, a series of image data is acquired with an MRI system by applying RF energy at the labeling spectral line changing incrementally, for example from down-field 204 to up-field 206 of water resonance. If the labeling spectral line is applied at the resonance frequency of the exchangeable proton, the saturation of the exchangeable protons is transferred through chemical exchange processes to nearby water protons, as indicated by line 208 in FIG. 1B. As a result, the detectable signal from these water protons is reduced. Referring now to FIG. 2C, there is no saturation transferred to the adjacent water spins and, therefore, no resultant decrease in detectable signal. In this manner, a so-called "Z spectrum" is acquired.

The present disclosure recognizes that CEST imaging can provide clinical utility beyond the brain, such as when imaging other organs, including the heart or kidneys. That is, the present disclosure recognizes that pH estimated from CEST imaging to provide useful metabolic information, for example, to accompany conventional perfusion and diffusion MRI studies. However, CEST MRI suffers from several limitations including long image acquisition times and the qualitative nature of the CEST contrast, which depends on many factors, including the chemical exchange rate, concentration of exchangeable protons, longitudinal relaxation time, and RF saturation power. Trying to extend CEST MRI pulse sequence to, for example, heart applications is challenging. Even with proper cardiac gating, motion artifacts can be present with CEST MRI because CEST pulse sequences utilize a relatively long saturation time. Although the initiation of the saturation is triggered, a slight shift in cardiac rate/signal can cause misalignment at the time of acquisition, causing appreciable motion artifacts in the resulting images. Positioning the trigger before image acquisition, the post-labeling delay may vary substantially, which results in non-CEST contamination to the images.

Figure 2D:
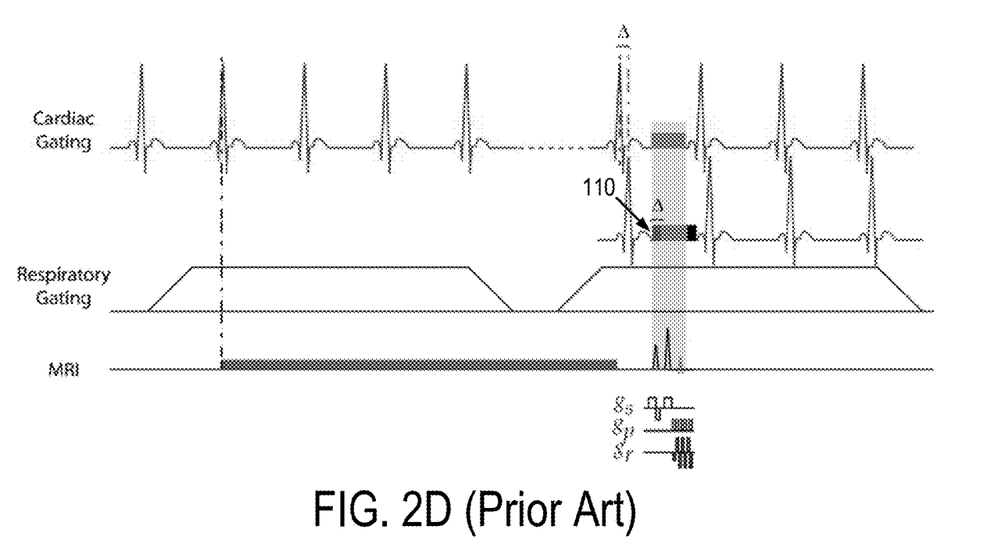
FIG. 2D is a pulse sequence diagram of a traditional CEST acquisition showing some of the challenges presented by CEST imaging in cardiac applications.

In particular, referring to FIG. 2D, a pulse sequence diagram is provided for the conventional, cardiac-gated CEST MRI. As illustrated, any shift, even a subtle shift, in the cardiac rate during the scan time causes motion artifacts. As shown in FIG. 2D, the conventional cardiac-gated CEST MRI includes a relatively long saturation time (e.g., a saturation that occurs over multiple R-R intervals in an EKG) followed by an acquisition. Although the initiation of the saturation is triggered, if the cardiac period is shifted by time of Δ, the acquisition will be equivalent to starting earlier in time by an amount 110 equal to Δ and, thereby, the acquisition will terminate early. Unfortunately, such shifts are not uncommon in patients due to a change in the patient's cardiac rate or arrhythmias. Notably, this artifact is not only observable in animal cardiac imaging due to its high cardiac rate, but also common in large animals and humans. Shifts, such as Δ, lead to significant motion artifacts while using conventional cardiac-gated CEST MRI.

To overcome the aforementioned drawbacks, the present disclosure provides a pulse sequence herein referred to as separately triggered irradiation and excitation (STRIDE) CEST MRI. The STRIDE CEST MRI sequence utilizes a secondary gating to reset or adjust the imaging acquisition with respect to a second trigger point in a physiological signal, and, therefore, controls motion artifacts. This allows for CEST images, such as a pH map, creatine map, and the like, to be generated from CEST RF saturation pulses without significant motion artifacts induced by a mild change in cardiac rate and/or arrhythmia.

Figure 3:
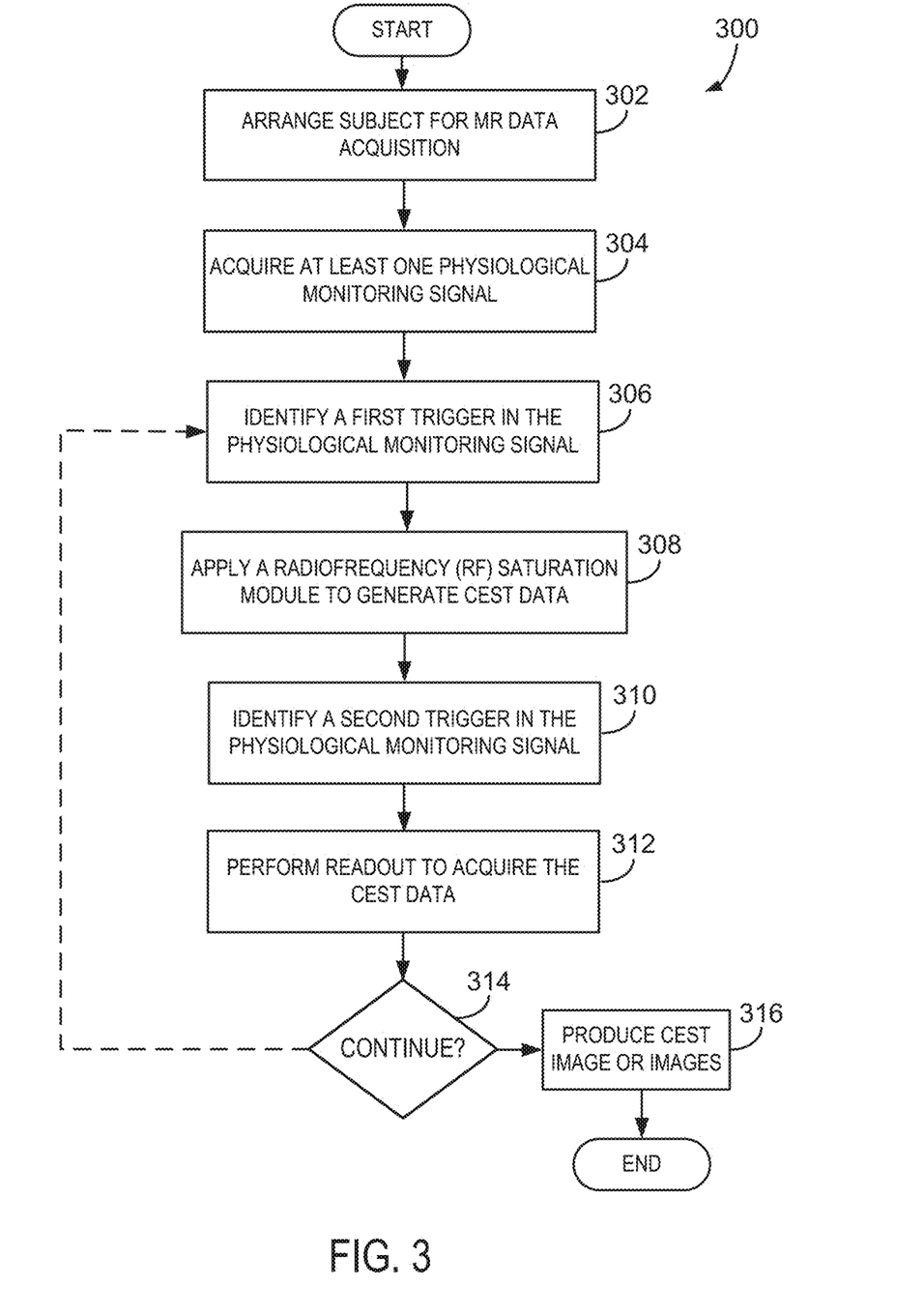
FIG. 3 is a flowchart illustrating one non-liming example of a CEST imaging technique in accordance with the present disclosure.

Referring to FIG. 3, a flow chart is provided that provides some, non-limiting example steps of a process for applying a STRIDE CEST MRI sequence to produce a CEST image of a subject in accordance with the present disclosure. The process 300 beings at process block 302 by arranging the subject in a magnetic resonance (MR) system capable of acquiring MR data from a region-of-interest of the subject. Arranging the subject 302 may also include arranging a physiological monitoring device to the subject to monitor physiological signals during imaging, such as an electrocardiogram (EKG) for measuring cardiac signals or a plethysmograph for monitoring respiratory signals. Other suitable physiological monitoring devices include, but are not limited to, an electromyogram (EMG), electroculogram (EOG), electrogastrogram (EGG), temperature, electrodermal activity (EDA, EDR, SCL, SCR or GSR), hand grip strength (dynamometry), $CO_2$ and $O_2$ gas analysis, pulse oximeter, and the like.

As indicated at 304, the process 300 includes acquiring at least one physiological monitoring signal of the subject that relates to at least one physiological process. For example, a single physiological signal may be used, such as one related only to cardiac cycle or respiration. Additionally or alternatively, two physiological signals may be monitored that are both related to the same underlying physiological process or cycle, such as two monitors that provide physiological signals that are both related to the cardiac cycle or both related to respiration. The process 300 proceeds by identifying a first trigger point 306 by analyzing the physiological monitoring signal, and upon identifying the first trigger point, applying a radiofrequency (RF) saturation module at a selected frequency or range of frequencies to saturate at least a selected spin species in the subject to generate CEST data. Alternatively, upon identifying the first trigger point, the process may proceed by applying a RF saturation module to generate magnetization transfer (MT) or arterial spin labeling (ASL) data.

The RF irradiation is typically applied in increments or offset by offset using a continuous-wave saturation pulse or a train of RF saturation pulses. In one aspect, the RF irradiation may be applied over the duration of multiple EKG signals (e.g., 2, 4, 16, 32, etc), which are typically defined by an interval between R-waves, also known as an R—R interval. In one example, the RF pulse is applied in a series of saturation modules (continuous-wave or a train of saturation pulses) that are timed to coincide with a part of the cardiac cycle that has more uniform magnetic field, for example, a diastole phase.

As indicated at 310, a second trigger point is then identified by analyzing the physiological monitoring signal, and upon identifying the second trigger point, performing a chemical exchange saturation transfer (CEST) readout 312 to acquire CEST data. For example, to accommodate for changes in a patient's cardiac cycle or arrhythmias, the timing of the acquisition window or the duration of the saturation module may be adjusted based on the timing of the second trigger point in the physiological monitoring signal. In one non-limiting example, the RF saturation module may be configured to be of a predetermined duration from the first trigger and the RF saturation module may then be reduced or extended before the second trigger so that the image readout is gated by the second trigger. This process advantageously allows for a long saturation and synchronized acquisition to generate CEST data having motion artifacts reduced. As indicated by decision block 314, the process steps 306-312 may be optionally repeated for multi-slice acquisition and imaging. If the decision is made to not repeat process steps 306-312, then the process may proceed to reconstructing the CEST data to produce a CEST image of the subject 316.

Figure 4A:
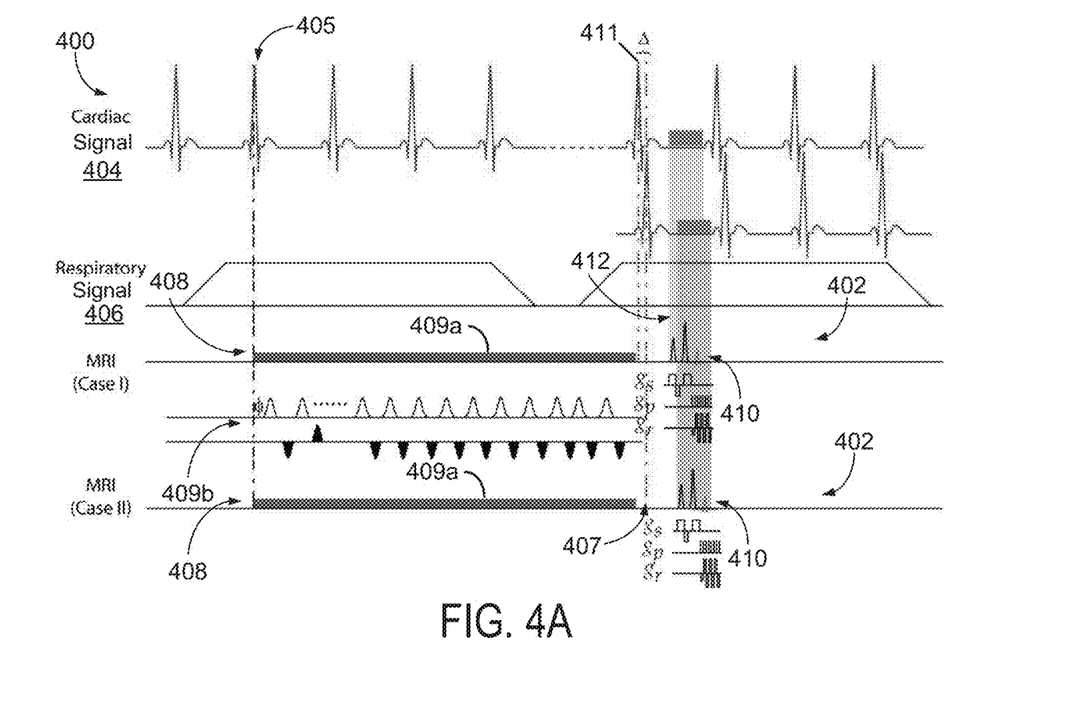
FIG. 4A is a pulse sequence diagram illustrating one non-limiting example of a CEST imaging technique in accordance with the present disclosure.

To further illustrate the STRIDE CEST MRI sequence, one non-limiting example of a pulse sequence is provided in FIG. 4A in accordance with the present disclosure. More particularly, FIG. 4A an example that includes applying respiratory and/or cardiac gating to control the CEST saturation and image acquisition during a STRIDE CEST MRI sequence.

Specifically, referring to FIG. 4A, STRIDE CEST MRI, in a fundamental form, provides a method 400 employing a CEST pulse sequence 402 that utilizes two physiological monitoring signals 404, 406, which in this non-limiting example include cardiac and respiratory signals 404 and 406. These two physiological signals 404, 406 can be used to generate two triggers 405, 407. In particular, in accordance with this non-limiting example, a first trigger 405 is executed upon determining at least one predetermined indicator in the physiological monitoring signals 404, 406. In this non-limiting example of a cardiac signal 404 and respiratory signal 406, the predetermined indicator may be concurrent synchronization in the cardiac and respiratory cycles. Additionally or alternatively, the first trigger 405 may be executed based on only one of the physiological signals 404 or 406, or the physiological signals may be monitoring different physiological functions, other than respiration and cardiac cycles.

The first trigger 405 may be used to initiate part of the CEST pulse sequence 402. As one non-limiting example, as illustrated, the first trigger 405 may be used to initiate a CEST saturation module 408. As will be further described, the saturation module 408 may be formed by a continuous-wave 409a or a train of saturation pulses 409b. The duration of the saturation module 408 may be determined based on the physiological signals 404, 406, such as cardiac rate and/or respiratory rate, so the saturation module 408 terminates before relative to an intended cardiac cycle and/or respiratory cycle, and/or time. To achieve this, the CEST data readout 410 is initiated based on the second trigger 407. In one non-limiting example, the second trigger 407 may correspond to an R-wave 411 in a cardiac signal, since this is usually the most prominent feature of an EKG.

As illustrated, the saturation module 408, which is needed for CEST data readout 410, is substantially longer in duration than any Δ value. Thus, any value of Δ and a corresponding extension or contraction of the saturation module 408 or adjustment to the timing 412 of the remainder of the pulse sequence 402 does not affect the effectiveness of the saturation module 408 on achieving proper CEST data readout 410. In addition, Δ can be recorded to correct for its impact on the magnitude/phase of MRI contrast. The extension of contraction of the saturation module 408 can be performed based on an anticipated timing of the second trigger 407 based on ongoing monitoring of the physiological signals 404, 406. In fact, the duration of the adjustment to the saturation module 408 or timing of the remainder of the pulse sequence 402 does not need to exactly match the value of Δ. For example, the second trigger 407 can be selected for a time when the physiological signals are best aligned, which could be offset some from the duration of Δ. Alternatively, the duration of the saturation module 408 can be extended until the second trigger 407.

While the above-described example utilizes two different physiological signals 404, 406, a single signal or two signals related to the same underlying physiological cycle may be used. For example, a single physiological signal may be used, such as one related only to cardiac cycle or respiration. Additionally or alternatively, two physiological signals may be monitored that are both related to the same underlying physiological cycle, such as two monitors that provide physiological signals that are both related to the cardiac cycle or both related to respiration. Furthermore, more than two physiological signals may be monitored and used for generating the triggers.

In many cases, it is advantageous to have the second trigger 407 occur at a desired time. While in practice, the second trigger 407 may shift slightly due to the variation in cardiac rate, the overall scan time is comparatively long, which provides flexibility to reset or adjust the timing of the saturation module 408 and CEST data readout 410. For example, cardiac pH and creatine maps may be obtained from STRIDE cardiac CEST MRI without worrying about mild variation in cardiac rate and/or due to arrhythmia that may be common in patients.

Figure 4B:
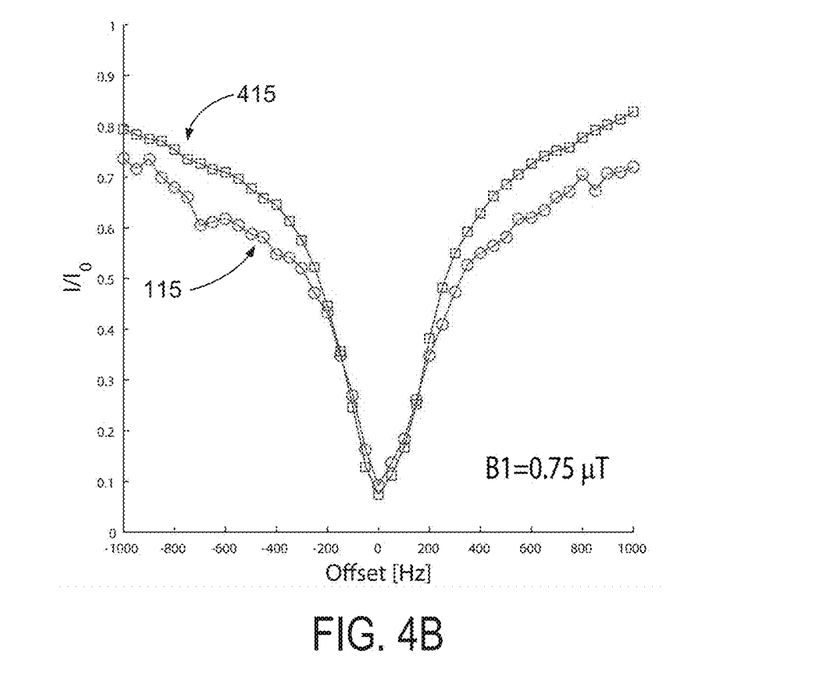
FIG. 4B is a graph comparing the results of CEST data acquired in accordance with the present disclosure.

Referring to FIG. 4B, a comparison is illustrated of a Z-spectra 115 obtained from the conventional single-gated CEST acquisition of FIG. 1D, and a Z-spectra 415 obtained from the above-described double-gated STRIDE CEST technique is provided. The conventional approach has low reproducibility due to poor synchronization between image acquisition and cardiac cycle. In comparison, the "double gated" STIDE CEST Z-spectra 415 shows a stable CEST Z-spectrum, clearly revealing both an amide attributed to the APT effect at 3.5 ppm (pH sensitive) and a creatine signal at 1.9 ppm (pH sensitive).

Figure 4C:
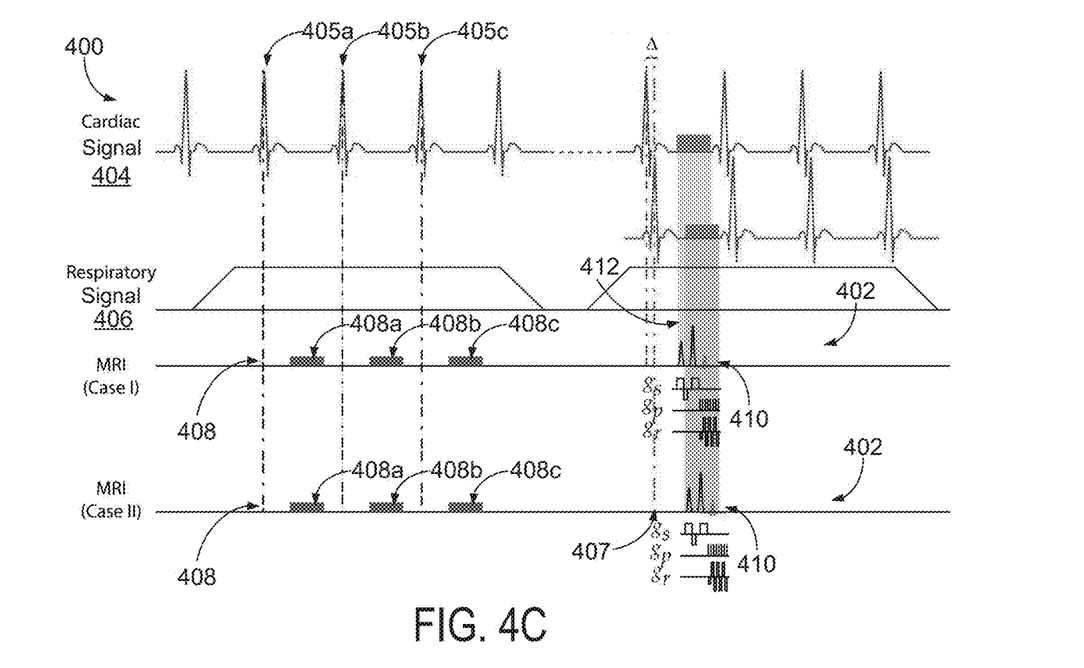
FIG. 4C is a pulse sequence diagram illustrating another non-limiting example of a CEST imaging technique in accordance with the present disclosure.

The above-described STRIDE CEST MRI technique can be modified in a variety of different ways to achieve particular clinical goals. For example, referring to FIG. 4C, during the cardiac cycle, the heart may experience different field inhomogeneity. Thus, it may be advantageous for this or other reasons to gate the saturation module 408 to be performed by a series of saturation modules (continuous-wave or a train of saturation pulses) 408a, 408b, 408c that are timed to coincide with a part of the cardiac cycle that has more uniform magnetic field, for example, a diastole phase. In this case, the first trigger 405 may be performed with a series of triggers points 405a, 405b, 405c. In effect, the first trigger point 405 described above with respect to FIG. 4A is adjusted to perform multiple sub-trigger points 405a, 405b, 405c to turn the single, trigger-controlled, continuous-wave (CW) RF saturation pulse forming the saturation module 408 of FIG. 4A with multiple triggers-controlled saturation pulses 408a, 408b, 408c forming the overall saturation module followed by second (or nth) trigger-controlled acquisition 410.

The above-described STRIDE CEST MRI technique can be extended for fast multi-slice acquisition by adding multiple ECG-synchronized secondary CEST saturation and image readouts, as described at decision block 314 in FIG. 3. The multiple gating will keep the image acquisition under constant check and balance, ultimately permitting assessment metabolic status of the whole heart. More particularly, referring to FIG. 4D, the above-described STRIDE CEST MRI technique may be extended with secondary saturation and segmented multi-slice imaging to synchronize a CEST preparation pulse with multiple multi-slice acquisition. This can also be combined with simultaneous-multi-slice (SMS) imaging. The timing of saturation and acquisition can be triggered in and triggered out in this case for fast, large volume, such as whole heart, CEST imaging.

Figure 4D:
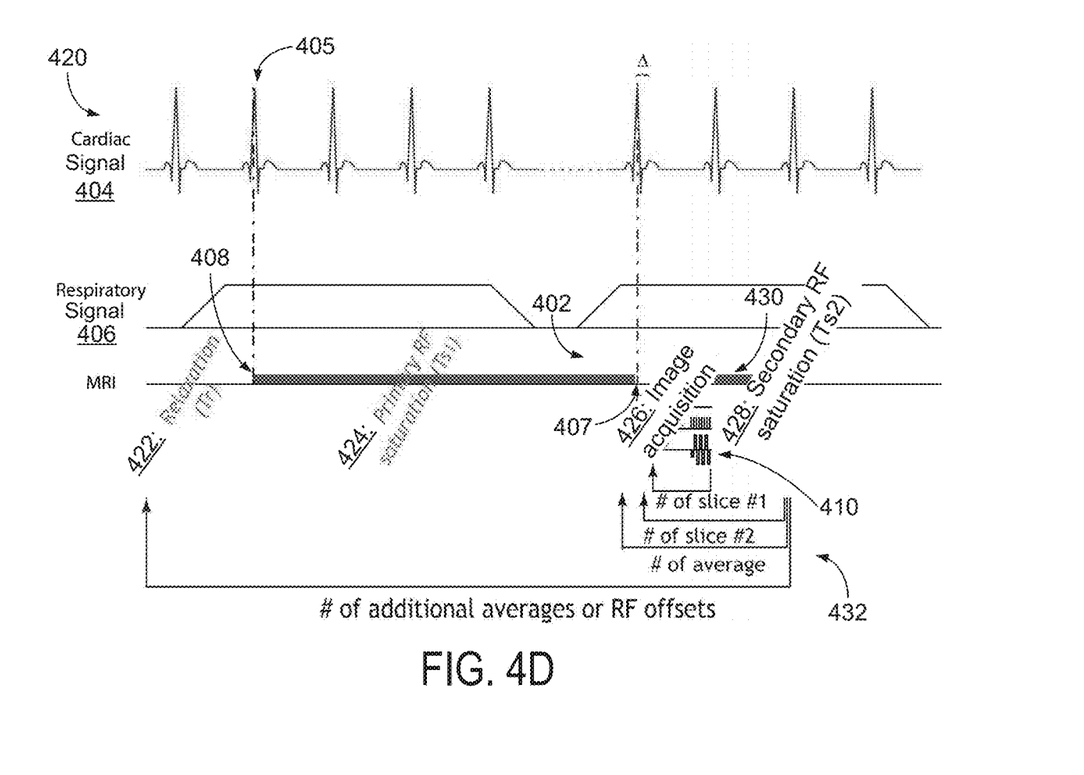
FIG. 4D is a pulse sequence diagram illustrating another non-limiting example of a CEST imaging technique in accordance with the present disclosure.

Specifically, referring to FIG. 4D, the pulse sequence described above with respect to FIG. 4A has been adapted to form a multi-slice STRIDE CEST pulse sequence 420. The multi-slice STRIDE CEST pulse sequence 420 can be conceptualized as including four sub-parts, including a relaxation period 422, a primary RF saturation period 424, an image acquisition period 426, and a secondary RF saturation period 428. The relaxation period 422 is characterized by being devoid of RF excitation to allow the magnetization from a prior slice to relax prior to application of a subsequent saturation module 408 in the following primary RF saturation period 424 initiated based on the first trigger 405. As described above, the second trigger 407 coordinates the end of the saturation module 408 and the beginning of the image acquisition period 426 and readout 410. Following readout 410, a secondary RF saturation module 430 is applied during the secondary RF saturation period 428. As indicated 432, this process occurs for each slice or multiple slices. In this way, a few slices (slice # 1) may be obtained after a single occurrence of the second trigger 407, and the process loops back to complete acquisition of all desired slices. In this way, the total scan time can be reduced. This implementation can be advantageous to cardiac imaging where the ECG cycle is relatively long.

Of course, the above-described STRIDE CEST techniques are not limited to cardiac applications. That is, the above-described techniques may be used to acquire CEST image of organs that are located within an abdomen of the subject. For example, the STRIDE CEST techniques can also be applied to CEST imaging of other tissues, systems, or organs such as kidney and liver, where triggering is desirable. In such other applications, it may be desirable to use different physiological signals for triggering.

Figure 5:
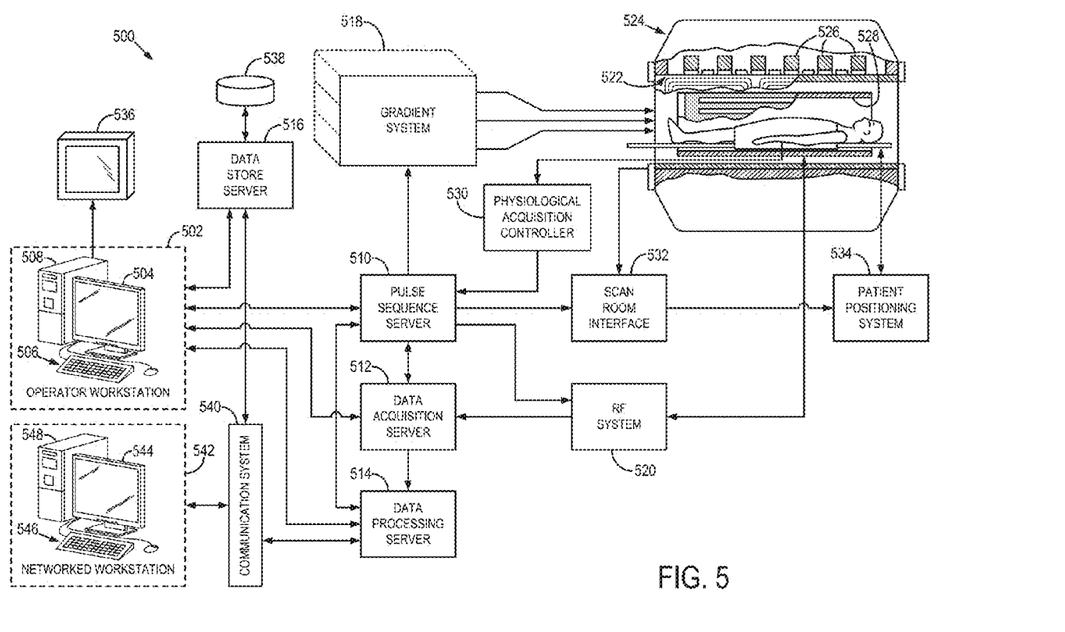
FIG. 5 is a block diagram of an example magnetic resonance imaging ("MRI") system that is configured to implement methods described here.

Referring particularly now to FIG. 5, an example of a magnetic resonance imaging ("MR") or nuclear magnetic resonance (NMR) system 500 that can implement the methods described here is illustrated. The MR system 500 includes an operator workstation 502 that may include a display 504, one or more input devices 506 (e.g., a keyboard, a mouse), and a processor 508. The processor 508 may include a commercially available programmable machine running a commercially available operating system. The operator workstation 502 provides an operator interface that facilitates entering scan parameters into the MR system 500. The operator workstation 502 may be coupled to different servers, including, for example, a pulse sequence server 510, a data acquisition server 512, a data processing server 514, and a data store server 516. The operator workstation 502 and the servers 510, 512, 514, and 516 may be connected via a communication system 540, which may include wired or wireless network connections.

The pulse sequence server 510 functions in response to instructions provided by the operator workstation 502 to operate a gradient system 518 and a radiofrequency ("RF") system 520. Gradient waveforms for performing a prescribed scan are produced and applied to the gradient system 318, which then excites gradient coils in an assembly 522 to produce the magnetic field gradients $G_x$, $G_y$, and $G_z$ that are used for spatially encoding magnetic resonance signals. The gradient coil assembly 522 forms part of a magnet assembly 524 that includes a polarizing magnet 526 and a whole-body RF coil 528.

RF waveforms are applied by the RF system 520 to the RF coil 528, or a separate local coil to perform the prescribed magnetic resonance pulse sequence. Responsive magnetic resonance signals detected by the RF coil 528, or a separate local coil, are received by the RF system 520. The responsive magnetic resonance signals may be amplified, demodulated, filtered, and digitized under direction of commands produced by the pulse sequence server 510. The RF system 520 includes an RF transmitter for producing a wide variety of RF pulses used in MR pulse sequences. The RF transmitter is responsive to the prescribed scan and direction from the pulse sequence server 510 to produce RF pulses of the desired frequency, phase, and pulse amplitude waveform. The generated RF pulses may be applied to the whole-body RF coil 528 or to one or more local coils or coil arrays. In one aspect, the RF system 520 may be configured to apply the RF saturation module described above in a series of RF saturation pulses timed based on respective ones of the series of sub-trigger points.

The RF system 520 also includes one or more RF receiver channels. An RF receiver channel includes an RF preamplifier that amplifies the magnetic resonance signal received by the coil 528 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 510 may receive patient data from a physiological acquisition controller 530. By way of example, the physiological acquisition controller 530 may receive signals from a number of different sensors connected to the patient, including electrocardiograph ("ECG") signals from electrodes, or respiratory signals from a respiratory bellows or other respiratory monitoring devices. These signals may be used by the pulse sequence server 510 to synchronize, or "gate," the performance of the scan with the subject's heart beat or respiration. In one non-limiting example, the physiological acquisition controller 530 may receive information from a cardiac monitor configured to generate a cardiac monitoring waveform. The physiological acquisition controller 530 may transfer these signals to the operator workstation 502, which may be configured to analyze the cardiac monitoring waveform to determine the first trigger point and/or second trigger point. Similarly, the physiological acquisition controller 530 may receive information from a respiration monitor configured to generate a respiration monitoring waveform. The physiological acquisition controller 530 may transfer these signals to the operator workstation 502, which may be configured to analyze the respiration monitoring waveform to determine the first trigger point and/or second trigger point. The RF system 520 may be configured to adjust a duration of the RF saturation module based on a timing, or an anticipated timing of a second trigger point.

The pulse sequence server 510 may also connect to a scan room interface circuit 532 that receives signals from various sensors associated with the condition of the patient and the magnet system. Through the scan room interface circuit 532, a patient positioning system 534 can receive commands to move the patient to desired positions during the scan.

The digitized magnetic resonance signal samples produced by the RF system 520 are received by the data acquisition server 512. The data acquisition server 512 operates in response to instructions downloaded from the operator workstation 502 to receive the real-time magnetic resonance data and provide buffer storage, so that data is not lost by data overrun. In some scans, the data acquisition server 512 passes the acquired magnetic resonance data to the data processor server 514. In scans that require information derived from acquired magnetic resonance data to control the further performance of the scan, the data acquisition server 512 may be programmed to produce such information and convey it to the pulse sequence server 510. For example, during pre-scans, magnetic resonance data may be acquired and used to calibrate the pulse sequence performed by the pulse sequence server 510. As another example, navigator signals may be acquired and used to adjust the operating parameters of the RF system 520 or the gradient system 518, or to control the view order in which k-space is sampled. In still another example, the data acquisition server 512 may also process magnetic resonance signals used to detect the arrival of a contrast agent in a magnetic resonance angiography ("MRA") scan. For example, the data acquisition server 512 may acquire magnetic resonance data and processes it in real-time to produce information that is used to control the scan.

The data processing server 514 receives magnetic resonance data from the data acquisition server 512 and processes the magnetic resonance data in accordance with instructions provided by the operator workstation 502. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 514 are conveyed back to the operator workstation 502 for storage. Real-time images may be stored in a data base memory cache, from which they may be output to operator display 502 or a display 536. Batch mode images or selected real time images may be stored in a host database on disc storage 538. When such images have been reconstructed and transferred to storage, the data processing server 514 may notify the data store server 516 on the operator workstation 502. The operator workstation 502 may be used by an operator to archive the images, produce films, or send the images via a network to other facilities.

The MR system 500 may also include one or more networked workstations 542. For example, a networked workstation 542 may include a display 544, one or more input devices 546 (e.g., a keyboard, a mouse), and a processor 548. The networked workstation 542 may be located within the same facility as the operator workstation 502, or in a different facility, such as a different healthcare institution or clinic.

The networked workstation 542 may gain remote access to the data processing server 514 or data store server 516 via the communication system 540. Accordingly, multiple networked workstations 542 may have access to the data processing server 514 and the data store server 516. In this manner, magnetic resonance data, reconstructed images, or other data may be exchanged between the data processing server 514 or the data store server 516 and the networked workstations 542, such that the data or images may be remotely processed by a networked workstation 542.

The present disclosure has described one or more preferred embodiments, and it should be appreciated that many equivalents, alternatives, variations, and modifications, aside from those expressly stated, are possible and within the scope of the invention.

The invention claimed is:

1. A method for producing a magnetic resonance (MR) image of a subject, the method including steps comprising:
   a) acquiring a first physiological monitoring signal related to a first physiological process of the subject;
   b) acquiring a second physiological monitoring signal related to a second physiological process of the subject;
   c) analyzing the first physiological monitoring signal and the second physiological monitoring signal to identify at least a first trigger point and a second trigger point;
   d) upon identifying the first trigger point, applying a radiofrequency (RF) saturation module at a selected frequency or range of frequencies to saturate at least a selected spin species in the subject;
   e) upon identifying the second trigger point, performing a chemical exchange saturation transfer (CEST) readout to acquire CEST data;
   f) reconstructing the CEST data to produce a CEST image of the subject, and
   wherein step d) further includes adjusting a duration of the RF saturation module based on an anticipated timing of the second trigger point, and
   wherein the duration of the RF saturation module is extended or contracted based on the anticipated timing of the second trigger point, and the anticipated timing of the second trigger point is determined based on ongoing monitoring of the first physiological signal and the second physiological signal.

2. The method of claim 1 wherein the first physiological process includes a cardiac or respiratory cycle of the subject.

3. The method of claim 1 wherein the second physiological process includes at least one of a cardiac or respiratory cycle of the subject.

4. The method of claim 1 wherein the CEST image includes an organ of the subject located within an abdomen or chest of the subject.

5. The method of claim 1 wherein steps e)-f) form a multi-slice acquisition.

6. The method of claim 5 wherein the multi-slice acquisition is a simultaneous multi-slice acquisition.

7. The method of claim 1 wherein the first trigger point is formed by a series of sub-trigger points and wherein the RF saturation module is formed by a series of RF saturation pulses timed based on respective ones of the series of sub-trigger points.

8. The method of claim 1 wherein the RF saturation module is formed using a continuous wave RF saturation pulse.

9. The method of claim 1, wherein the RF saturation module is offset from the second trigger point.

10. A system comprising:
   a magnet system configured to generate a polarizing magnetic field about at least a portion of a subject;
   a magnetic gradient system including a plurality of magnetic gradient coils configured to apply at least one magnetic gradient field to the polarizing magnetic field;
   a radio frequency (RF) system configured to apply an RF field to the subject and to receive magnetic resonance signals from the subject using a coil array;
   a computer system programmed to:
      analyze a first physiological monitoring signal related to a first physiological process of the subject and a second physiological monitoring signal related to a second physiological process of the subject to identify at least a first trigger point and a second trigger point;
      upon identifying the first trigger point, control the RF system to applying a radiofrequency (RF) saturation module at a selected frequency or range of frequencies to saturate at least one selected spin species in the subject;
      upon identifying an occurrence of the second trigger point, control the magnetic gradient system and the RF system to acquire chemical exchange saturation transfer (CEST) data from the subject; and reconstruct the CEST data to produce an image of the subject,
   wherein controlling the RF system to applying a radiofrequency (RF) saturation module further includes adjusting a duration of the RF saturation module based on an anticipated timing of the second trigger point, and
   wherein the duration of the RF saturation module is extended or contracted based on the anticipated timing of the second trigger point, and the anticipated timing of the second trigger point is determined based on ongoing monitoring of the first physiological signal and the second physiological signal.

11. The system of claim 10 wherein the CEST data includes magnetization transfer (MT) or arterial spin labeling (ASL) data.

12. The system of claim 10 further comprising a cardiac monitor configured to generate a cardiac monitoring waveform and wherein the computer system is further configured to analyze the cardiac monitoring waveform to determine the first trigger point.

13. The system of claim 10 further comprising a respiration monitor configured to generate a respiration monitoring waveform and wherein the computer system is further configured to analyze the respiration monitoring waveform to determine the second trigger point.

14. The system of claim 10 wherein the image includes an organ of the subject located within an abdomen or chest of the subject.

15. The system of claim 10 wherein the computer is configured to acquire the CEST data according to a multi-slice acquisition.

16. The system of claim 15 wherein the multi-slice acquisition is a simultaneous multi-slice acquisition.

17. The system of claim 10 wherein the first trigger point is formed by a series of sub-trigger points and wherein the RF saturation module is formed by a series of RF saturation pulses timed based on respective ones of the series of sub-trigger points.

18. The system of claim 10 wherein the RF saturation module is formed using a continuous wave RF saturation pulse.

* * * * *